United States Patent
Li et al.

(10) Patent No.: US 10,383,330 B2
(45) Date of Patent: Aug. 20, 2019

(54) ANTIMICROBIAL COMPOSITIONS AND METHODS OF USE

(71) Applicant: Purdue Research Foundation, West Lafayette, IN (US)

(72) Inventors: Jianming Li, Lafayette, IN (US); Sean Dennis Connell, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/775,865

(22) PCT Filed: Mar. 13, 2014

(86) PCT No.: PCT/US2014/025752
§ 371 (c)(1),
(2) Date: Sep. 14, 2015

(87) PCT Pub. No.: WO2014/151449
PCT Pub. Date: Sep. 25, 2014

(65) Prior Publication Data
US 2016/0007594 A1 Jan. 14, 2016

Related U.S. Application Data

(60) Provisional application No. 61/794,661, filed on Mar. 15, 2013.

(51) Int. Cl.
| | | |
|---|---|---|
| *A01N 25/30* | (2006.01) | |
| *A61K 8/06* | (2006.01) | |
| *A61L 15/00* | (2006.01) | |
| *A61K 9/10* | (2006.01) | |
| *A23B 7/00* | (2006.01) | |
| *A61K 47/10* | (2017.01) | |
| *A61L 26/00* | (2006.01) | |
| *A61K 8/34* | (2006.01) | |
| *A01N 25/22* | (2006.01) | |
| *A01N 31/14* | (2006.01) | |
| *A01N 31/08* | (2006.01) | |
| *A01N 31/16* | (2006.01) | |
| *A01N 25/04* | (2006.01) | |

(52) U.S. Cl.
CPC ............ *A01N 25/30* (2013.01); *A01N 25/04* (2013.01); *A01N 25/22* (2013.01); *A01N 31/08* (2013.01); *A01N 31/14* (2013.01); *A01N 31/16* (2013.01); *A23B 7/00* (2013.01); *A61K 8/06* (2013.01); *A61K 8/347* (2013.01); *A61K 9/10* (2013.01); *A61K 47/10* (2013.01); *A61L 15/00* (2013.01); *A61L 26/00* (2013.01); *A61L 26/0061* (2013.01)

(58) Field of Classification Search
CPC ........ A01N 25/30; A01N 31/14; A01N 25/22; A01N 31/08; A01N 31/16; A01N 25/04; A61K 8/06; A61K 9/10; A61K 47/10; A61K 8/347; A61L 15/00; A61L 26/00; A61L 26/0061; A23B 7/00
See application file for complete search history.

(56) References Cited

U.S. PATENT DOCUMENTS

| | | | |
|---|---|---|---|
| 5,403,587 A | 4/1995 | McCue et al. | |
| 6,585,961 B1 | 7/2003 | Stockel | |
| 6,723,364 B1 * | 4/2004 | Bompeix ............... | A01N 31/16 426/102 |
| 6,884,763 B2 | 4/2005 | Willard et al. | |
| 7,341,736 B2 * | 3/2008 | Flashinski ............. | A01N 25/06 424/405 |
| 2005/0014449 A1 * | 1/2005 | Pascual .................. | A01N 65/22 449/3 |
| 2008/0075794 A1 | 3/2008 | Bae | |
| 2009/0269394 A1 | 10/2009 | Baker, Jr. et al. | |
| 2010/0092526 A1 | 4/2010 | Baker, Jr. et al. | |
| 2012/0003163 A1 | 1/2012 | Mordas et al. | |
| 2012/0276182 A1 | 11/2012 | Baker, Jr. et al. | |

FOREIGN PATENT DOCUMENTS

| | | | |
|---|---|---|---|
| CN | 101214355 A | 7/2008 | |
| WO | 2007133934 A1 | 11/2007 | |
| WO | WO-2007133934 A1 * | 11/2007 | ............. C11D 1/662 |
| WO | 2012170841 A1 | 12/2012 | |

OTHER PUBLICATIONS

Ziani, K., Influence of Surfactant Charge on Antimicrobial Efficacy of Surfactant-Stabilized Thyme Oil Nanoemulsions, 2011, Journal of Agricultural and Food Chemistry, vol. 59, pp. 6247-6255. (Year: 2011).*

Buranasuksombat et al., Influence of emulsion droplet size on antimicrobial properties, Food Science and Biotechnology, vol. 20, No. 3, pp. 793-800, (2011).

* cited by examiner

*Primary Examiner* — John Pak
*Assistant Examiner* — Andriae M Holt
(74) *Attorney, Agent, or Firm* — Valauskas Corder LLC

(57) ABSTRACT

Disclosed are antimicrobial emulsions, products comprising the emulsions, and methods of use.

22 Claims, 2 Drawing Sheets

ANTIMICROBIAL COMPOSITIONS AND METHODS OF USE

CROSS-REFERENCE TO RELATED APPLICATIONS

This application claims the benefit of priority to U.S. Provisional Application No. 61/794,661, filed Mar. 15, 2013, which is incorporated by reference in its entirety.

STATEMENT REGARDING FEDERALLY SPONSORED RESEARCH OR DEVELOPMENT

Not applicable.

INTRODUCTION

There is a significant need for antimicrobial compositions that are not based on antibiotics commonly used today or which do not rely on harsh biocides detrimental to living tissue or the environment. Hospital-acquired infections are on the rise, including those caused by antibiotic-resistant pathogens, such as methicillin-resistant *Staphylococcus aureus* (MRSA). Treatment of hospital-acquired infections costs the United States health care system an estimated ten billions dollars annually. Another common source of infection is food contaminated with pathogenic bacteria. Infections caused by food-borne pathogens place significant burdens on human health and on the agricultural industry.

One important strategy used to prevent infections is treatment of surfaces that serve as a source of pathogens with disinfecting agents. Surface disinfecting agents or antiseptics have been used in both medical and non-medical applications. Although commercially available formulations have some efficacy against a variety of pathogenic microorganisms, many are toxic to humans upon contact with skin or other tissue, inhalation, or ingestion. Exposure to some antimicrobial formulations have serious, long-term health consequences.

Some synthetic chemical products leave potentially harmful residues that require removal from the surface to which the product is applied. For example, bleach, peroxides, chlorinated agents, formaldehydes and/or quaternary ammonium compounds pose toxicity concerns when deposited food contacting surfaces or on food items (e.g., produce, eggs). Therefore, the treated surface requires further washing to remove chemical residues. Such drawbacks limit the use of traditional chemical products in agriculture and food preparation.

Alternative products have been proposed for combating surface microbes. For example, essential oils or their derivatives are attractive alternatives. Essential oils have been used in a variety of surface cleansers, hand sanitizers, and wound treatment formulations. Many essential oils (e.g., thyme oil, oregano oil, and/or clove oil) possess antimicrobial activity and can be relatively benign to humans, and some are used as food additives. However, the volatility and hydrophobicity of essential oils, and variability in the essential oil compositions, present challenges in delivering these essential oils in a form suitable for widespread consumer use. For example, essential oils are insoluble in water, and phase separation results in an undesirable heterogeneous mixture. Many essential oils are often composite oils comprising a plurality of components, as they arise from plants, which can make the chemistry, and ultimately antimicrobial performance, somewhat variable, for example due to chemical differences from batch to batch. The lipid component in essential oils are susceptible to oxidation, which limits the shelf life of the oils. Additional preservatives may extend storage stability, but can add complexity and interfere with natural antimicrobial activity of the oils. Stabilizing surfactants, lipids, or preservatives can reduce the antimicrobial properties of essential oils. In some instances, antimicrobial formulations comprising essential oils can leave streaks or residues on the target surface, which can be aesthetically or tactilely displeasing, which can be especially important on glass, metal, and other surfaces with a glossy finish.

There is a need in the art for formulations based on natural antimicrobial products having improved stability and water miscibility, while retaining effective levels of antimicrobial activity. The present invention addresses that need.

SUMMARY OF THE INVENTION

In certain embodiments are provided antimicrobial formulations that include an active component, a surfactant, an organic co-solvent, and water. The active component is selected from monoterpenoids and polyphenols. The formulations are provided as an emulsion that have, in certain embodiments, an average emulsion particle or droplet size in the range of from about 25 nanometers (nm) to about 3000 nm.

In certain embodiments, active component is selected from the thymol, carvacrol, menthol, eugenol, cymene, p-cymene, limonene, geraniol, terpineol, eucalyptol, and citral.

In certain embodiments the surfactant is a non-ionic surfactant or an anionic surfactant. In certain embodiments, the surfactant is selected from polyoxyethylene glycols, polyoxypropylene glycols, glucosides, polyoxyethylene glycol octylphenol ethers, polyoxyethylene glycol alkylphenol ethers, glycerol alkyl esters, polysorbates, sorbitan esters (spans), cocamides, poloxamers, polyethoxylated tallow amines, sodiuim dodecyl sulfate (sodium lauryl sulfate), and ethoxylated sodium lauryl sulfate (sodium laureth sulfate), and combinations thereof.

In certain embodiments, the formulations include the active component and surfactant in ratio in the range of from about 1:5 and about 30:1.

In certain embodiments, the concentration of the surfactant in the formulation for use as an antimicrobial formulation is from about 0.0015% to about 0.1%. That the antimicrobial composition contains such a very low concentration of surfactant offers numerous advantages, including providing a product having a less soapy feel or texture, reducing the risk of skin irritation, contact dermatitis, and allergic reactions, and reducing the cost of manufacture. In certain embodiments, the antimicrobial formulations may be provided in a concentrated form for dilution prior to use. Such concentrated formulations will have higher concentrations of surfactant that formulation that can be used without prior dilution, but will have the same ratio of active component and surfactant as the ready to use formulation, i.e., the active component and surfactant in ratio in the range of from about 1:5 and about 30:1.

In certain embodiments, the co-solvent of the antimicrobial formulations is an organic polar co-solvent. In certain embodiments, the organic co-solvent is a short chain alcohol (e.g., methanol, ethanol, or butanol), a carboxylic acid (e.g., acetic acid or citric acid), acetone, methyl ethyl ketone, chloroform, DMSO, or an ether.

It is an advantage of the antimicrobial formulations of the invention that that the active components have improved solubility in aqueous solutions.

Another advantage of the antimicrobial formulations of the present invention is that the emulsion particles or droplets have a low polydispersity index (PDI). In certain embodiments, the PDI is in the range of from about 0.1 to about 0.5

It is a further advantage that the emulsions are relatively stable, even after being subjected to moderate heat treatment, freeze-thaw cycles, or centrifugation.

It is an advantage that the antimicrobial formulations are effective against a wide range of pathogens, including both gram positive and gram negative bacteria, antibiotic resistant bacteria, yeast and viruses.

It is a further advantage that the active component of the antimicrobial formulation is a natural product of very low toxicity.

It is an advantage that the antimicrobial formulations' of the invention are effective against planktonic microorganisms and biofilms.

The antimicrobial formulations of the present invention may be used in any method in which reduction in microorganisms is desired. The methods involve applying the object for which a reduction in microorganisms is desired in an amount and for a period of time effective to reduce microorganisms. Advantageously, the antimicrobial formulations may be used to disinfect hard surfaces, including, but not limited to, medical tools and devices, durable medical equipment, floors, walls, cutting boards, countertops, tabletops, toilet bowls, showers and bathtubs. The antimicrobial formulations may be used to disinfect food items, such as fruits, vegetables, including, for example, leafy green vegetables, and the shell of eggs. The antimicrobial formulations may be comprised within products such as cleaning solutions, disinfectants, sanitizers, antiseptics, wound care preparations, agricultural sprays or rinses, fruit and vegetable sprays for home use, and personal care products. The antimicrobial formulations may be used in personal care products such as cosmetics, antifungal creams, wound care preparations, toothpaste, oral rinses, and denture care products. Products may be provided to the end user in a concentrated form or in a pre-diluted, ready-to-use form.

The present invention and its attributes and advantages will be further understood and appreciated with reference to the detailed description below of presently contemplated embodiments and drawings.

DETAILED DESCRIPTION

Figure 1:
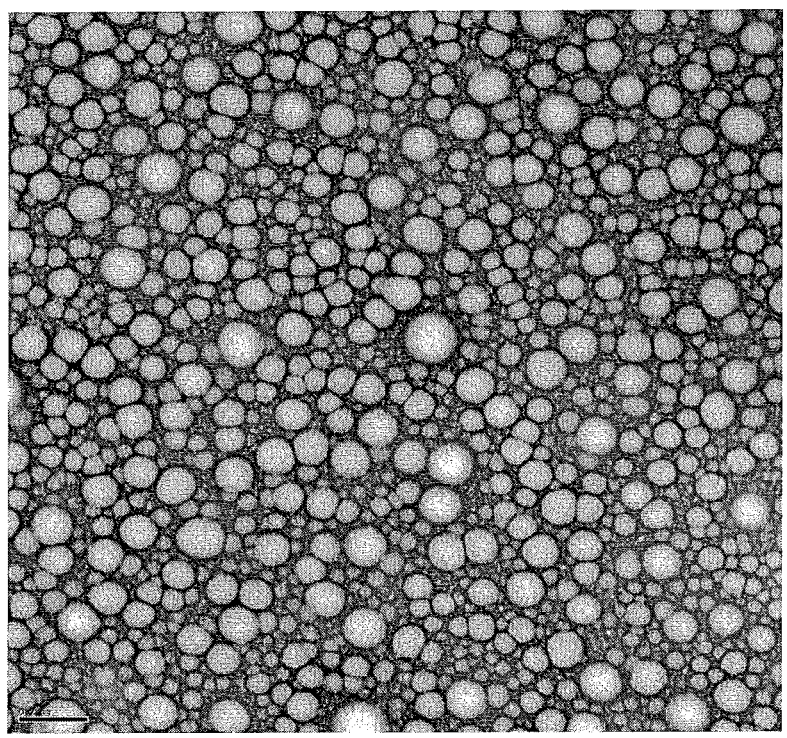
FIG. 1 is a transmission electron micrograph of a nanoemulsion comprising Tween 20 and thymol in a ratio of 1:10, and having an average droplet size of about 135 nm.

Although certain embodiments and examples are described below, those of skill in the art will appreciate that the disclosure extends beyond the specifically disclosed embodiments or uses and obvious modifications and equivalents thereof. Thus, it is intended that the scope of the disclosure herein provided should not be limited by any particular embodiments described below.

There exists a critical need for new types of natural antimicrobial formulations that are stable, water soluble, retain antimicrobial activity, and/or possess physical characteristics suitable for consumer and/or industrial use, for example including water soluble aqueous formulations that may be compatible with existing industrial and/or medical protocols. Such formulations may reduce the inappropriate and/or overuse of antibiotics, for example in the agricultural and/or medical fields.

In certain embodiments, the invention provides formulations comprising emulsions that include one or more active antimicrobial compounds including, for example, active antimicrobial compounds derived from essential oils. The antimicrobial compound or "active component", may include, without limitation, aromatic phenols derived from essential oils. In certain embodiments, the formulations may include water, for example, deionized water and/or distilled water, as a carrier medium. In certain embodiments, the active component may include one or more monoterpenoid and/or one or more polyphenols. In one embodiment the active component is selected from the group consisting of monoterpenoids and polyphenols. In some embodiments, the active component may include thymol, carvacrol, menthol, eugenol, cymene, p-cymene, limonene, geraniol, terpineol, eucalyptol, citral, or the like, and combinations thereof. In some embodiments, the active component is selected from the group consisting of thymol, carvacrol, menthol, eugenol, cymene, p-cymene, limonene, geraniol, terpineol, eucalyptol, and citral. Formulations can be free or substantially free of carrier oils and/or additional preservatives. Formulations can include a surfactant, including a non-ionic or anionic surfactant. For example, a formulation can include, as a surfactant, polyoxyethylene glycols, polyoxypropylene glycols, glucosides, polyoxyethylene glycol octylphenol ethers, polyoxyethylene glycol alkylphenol ethers, glycerol alkyl esters, polysorbates, sorbitan esters (spans), cocamides, poloxamers, polyethoxylated tallow amines, combinations thereof, and/or the like. In another example, the formulation is selected from the group consisting of polyoxyethylene glycols, polyoxypropylene glycols, glucosides, polyoxyethylene glycol octylphenol ethers, polyoxyethylene glycol alkylphenol ethers, glycerol alkyl esters, polysorbates, spans, cocamides, poloxamers and polyethoxylated tallow amines. Formulations can also include an anionic surfactant such as sodium dodecyl sulfate and sodium laureth sulfate. Formulations may further include a co-solvent, including an organic polar co-solvent. In some embodiments, a formulation can include as a co-solvent ethanol, methanol, acetic acid, acetone, methyl ethyl ketone, butanol, chloroform, DMSO, ether, citric acid, or the like, and combinations thereof. In some embodiments, the formulation includes a co-solvent selected from the group consisting of ethanol, methanol, acetic acid, acetone, methyl ethyl ketone, butanol, chloroform, DMSO, ether, citric acid. Additional carboxylic acid co-solvents may also be used.

In certain embodiments, the formulation is effective against a variety of microorganisms, for example microorganisms on a target surface. The formulation may be effective against bacteria, viruses and/or fungi. In certain embodiments, formulations of the invention are effective against microorganisms including, but not limited to, *Escherichia coli, Pseudomonas aeruginosa, Staphylococcus aureus* MRSA strains, *Enterococcus faecalis* VRE strain, *Candida albicans, Herpes simplex* 1, or the like, and/or combinations thereof. In certain embodiments, the formulations are effective against a microorganism selected from the group consisting of *Escherichia coli, Pseudomonas aeruginosa, Staphylococcus aureus* MRSA strain, *Enterococcus faecalis* VRE strain, Candida albicans, *Herpes simplex* 1, vancomycin resistant *Staphylococcus aureus* (VRSA), *Norovirus*, human immunodeficiency virus (HIV), *Rhinovirus*, *Clostridium difficile*, *Klebsiella pneumoniae*, *Mycobacterium tuberculosis*, *Salmonella typhimurium*, *Listeria monocytogenes*, *Vibrio cholera*, *Propionibacterium acnes*, and *Trichophyton mentagrophytes*.

In certain embodiments, the mean emulsion particle or droplet size or diameter is in the range of from nm to micrometers (μm). In certain embodiments, the mean particle size is from about 25 nm to about 5000 nm. In some embodiments, a mean emulsion droplet size can advantageously be less than 1000 nm. In certain embodiments, the mean emulsion droplet size is from about 25 nm to about 1000 nm. In some embodiments, the mean emulsion droplet size is from about 100 nm to about 600 nm. A formulation having a mean emulsion droplet size of less than about 1000 nm may exhibit improved shelf life properties, allowing extended storage of the formulation. In some embodiments, formulations having a mean emulsion droplet size less than about 1000 nm can be more easily distributed in an emulsion. For example, formulations having a mean emulsion droplet size less than about 1000 nm may facilitate a self-assembling emulsion, e.g., an emulsion that forms spontaneously or substantially spontaneously upon combining the components of the emulsion. In some embodiments, formulations having a mean emulsion droplet size less than about 1000 nm exhibit improved antimicrobial properties, for example, having improved ability to penetrate the skin and/or rough surface patches. A formulation having a mean emulsion droplet size less than about 1000 nm may have reduced viscosity, relative to formulations having larger mean emulsion droplet sizes. Formulations having reduced viscosity may be suitable for certain antimicrobial applications, including sprays, wipes, cleansers, flushes, wound preparations, and/or other similar applications.

A mean emulsion particle size can be controlled and/or filtered to satisfy different end user requirements. In some embodiments, a mean particle size can be controlled at least in part by a composition of the formulation. For example, formulations having compositions as described herein may exhibit mean emulsion droplet sizes suitable for a variety of applications. In some embodiments, formulations having compositions as described herein can provide, for example, desirable shelf life properties and/or antimicrobial properties. These include formulation having a composition as described herein may have a mean emulsion droplet size or particle size of less than about 1000 nm.

Because active components (e.g., phenolic compounds) are typically available as purified substances, chemical composition of an emulsion can be controlled, facilitating increased predictability in product performance. In some embodiments, formulations can comprise generally recognized as safe (GRAS) components, providing formulations suitable for animal and/or human consumption. Embodiments of antimicrobial emulsion liquids can be used on non-porous hard surfaces, washes for agricultural uses, animal feedstock and/or in direct contact with living tissues. In some embodiments, the antimicrobial emulsion can be used in disinfecting sprays, wipes, agricultural sanitizers, cleansers, flushes and/or as antimicrobial wound preparations.

Some embodiments relate to formulations comprising an emulsion which can be antimicrobial and can be used as, for example, surface cleansers, disinfectants, antiseptics, preservatives in animal feedstock and/or wound care preparations. Example formulations may comprise an active component, such as a phenolic compound derived from one or more essential oils, a non-ionic or anionic surfactant, a polar solvent, and/or water. Formulations may be manufactured using a self-assembly process, for example emulsions having a sub-micron mean emulsion particle size spontaneously or substantially spontaneously forming when ingredients are combined. The emulsions can be stable across a wide range of temperatures, have long storage life. In some embodiments, formulations can be effective antimicrobial agents against a host of pathogens, including for example, pathogenic bacteria, fungus, viruses and/or endospores. The compositions can be non-staining and/or streak free, without leaving oily or soapy residues on surfaces to which the compositions are applied.

In other embodiments, the antimicrobial liquids, when delivered in the "ready to use form" or an "end-user form" can advantageously comprise about 0.02% to about 1.00% by weight of an active component, including a monoterpenoid (e.g., thymol, carvacrol, and/or menthol) and/or a polyphenol (e.g., eugenol), a non-ionic or anionic surfactant in which the weight ratio of the active component to surfactant is between about 1:5 and about 30:1, a co-solvent comprising an organic compound, such as ethanol, at about 0.25% to about 15% by weight, and/or water, for example sufficient water to make up 100% by weight. A concentrated formulation can be manufactured in which the end-user can dilute the concentrated formulation into a desired final concentration. In some embodiments, a concentrated formulation can advantageously include about 1.0% to about 40% by weight of the active component (e.g., a monoterpenoid such as thymol, carvacrol, and/or menthol, and/or a polyphenol such as eugenol), a non-ionic surfactant in which the weight ratio of the active component to the surfactant is between about 1:5 and about 30:1, a co-solvent comprising an organic compound, such as ethanol, at about 10% to about 75% by weight, and/or water, for example sufficient water to make up 100% by weight.

In another embodiment, a formulation, for example used in disinfecting and antiseptic purposes, can include carvacrol between about 0.05% to about 0.10%, by weight. The formulation may have a surfactant, for example a polyoxyethylene 20 cetyl ether (e.g., Brij 58®), at a concentration of about 0.005% to about 0.01%, by weight, a co-solvent, for example an ethanol, at about 1% by weight, and/or water, for example distilled water making up the remaining weight. In some embodiments, a mean emulsion particle size of the formulation can be between about 25 nm to about 500 nm, with a PDI of between about 0.1 to about 0.5.

In an embodiment, a formulation, for example used in disinfecting and antiseptic purposes, can include thymol between about 0.05% to about 0.10%, by weight. The formulation may have a surfactant, for example a polysorbate 20, at a concentration of about 0.005% to about 0.01% by weight, a co-solvent, for example an alcohol at about 0.25% to about 2.0%, and/or water, for example distilled water making up the remaining weight. In some embodiments, a mean emulsion particle size can be between about 25 nm to about to about 500 nm, with a PDI of between about 0.1 to about 0.5.

In another embodiment, a formulation, for example used in disinfecting and antiseptic purposes, can include thymol between about 0.05% and about 0.10%, by weight. The formulation may have a surfactant, for example a polyoxyethylene 20 cetyl ether (e.g., Brij 58®), at a concentration of about 0.005% to about 0.01% by weight, a co-solvent, for example an alcohol, at about 0.5% to about 2.0% by weight, and/or water, for example distilled water making up the remaining weight. In some embodiments, a mean emulsion particle size can be between about 25 nm to about 900 nm, with a PDI of between about 0.1 to about 0.5.

In another embodiment, a formulation, for example used in disinfecting and antiseptic purposes, can include thymol between about 0.05% and about 0.10%. The formulation may include a surfactant, for example a sodium dodecyl sulfate, at a concentration of about 0.005% to about 0.01% by weight, a co-solvent, for example an alcohol, at about 0.5% to about 2.0% by weight, and/or water, for example distilled water making up the remaining. In some embodiments, a mean emulsion particle size can be between about 25 nm and about 600 nm, with a PDI of between about 0.1 to about 0.5.

In another embodiment, a formulation, for example used as an animal feed preservative, can include thymol between about 0.005% and about 0.10% by weight. The formulation can include a surfactant, for example a polysorbate 20, at a concentration of about 0.0015% to about 0.1% by weight, a co-solvent, for example an alcohol, at about 0.2% to about 1%, and/or water, for example distilled water making up the remaining weight. In some embodiments, a mean emulsion particle size can be between about 40 nm and about 1000 nm. In some embodiments, the formulation can be mixed into the foodstuffs.

In another embodiment, a formulation, for example used in disinfecting and antiseptic purposes, can include a carvacrol between about 0.05% and about 0.10% by weight. The formulation can include a surfactant, for example a polysorbate 20, at a concentration of about 0.005% to about 0.01% by weight, a co-solvent, for example an alcohol at about 1% by weight, and/or water, for example distilled water making up the remaining weight. In some embodiments, an emulsion particle size can be between about 25 nm and about 900 nm, with a PDI of between about 0.1 and about 0.5.

In some embodiments, a chelating agent, such as citric acid and/or ethylenediaminetetraacetic acid (EDTA), may be added to bind metal ions that may be present on the surfaces and/or other targets to which the formulation is applied. Chelators may be intended to enhance the binding affinity of the emulsion to the microorganism and/or be used as a water softening agent.

Certain embodiments may include more than one monoterpenoid and/or polyphenol combined in an emulsion form. For example, some embodiments may contain thymol at about 0.05% to about 0.10% by weight, and carvacrol at about 0.05% to about 0.10% by weight, mixed with a non-ionic surfactant and an alcohol co-solvent. Variations in the monoterpenoid and/or polyphenol compound type and/or mixture ratios are also envisioned.

In some embodiments, a fragrance and/or dye may be added to the emulsion in order to improve the olfactory characteristics and/or to impart color into the solution. These fragrances may include essential oils and/or their derivatives.

In another embodiment, a formulation, for example used in disinfecting and antiseptic purposes, can include eugenol between about 0.05% and about 0.10% by weight. The formulation can include a surfactant, for example a polysorbate 20, at a concentration of about 0.005% to about 0.01% by weight, a co-solvent, for example an alcohol, at about 0.25% to about 1% by weight, and/or water, for example distilled water to make up the remaining weight. In some embodiments, a mean emulsion particle size can be between about 40 nm and about 1000 nm, with a PDI of between about 0.1 and about 0.5.

In some embodiments, for example in formulations for disinfectant use, sporulating agents can be incorporated into the formulation to facilitate the germination of the spores and/or endospores into vegetative cells. The germinated cells can be subsequently inactivated by the formulation.

In some embodiments, surfactants used in the formulations can be of the edible nature, including for example polysorbates and/or lecithin, such that the formulations can be used for animal or human foodstuffs.

In some embodiments, the organic solvent (e.g., methanol, acetic acid, acetone, butanol, and/or chloroform) and/or the surfactant (e.g., Tween 80®, sodium laureth sulfate, sodium dodecyl sulfate, Brij®, and/or Triton X®) can be changed. Those skilled in the art will recognize that numerous modifications can be made to the specific implementations described above. Therefore, the following claims are not to be limited to the specific embodiments illustrated and described above. Some example compositions and corresponding data are shown in Table 1.

In some embodiments, antimicrobial emulsions can have the ability to reduce microorganism populations on contact with a variety of inanimate surfaces, living tissue and/or in foodstuffs. These microbes can include Gram-positive and/or Gram-negative bacteria, fungus, enveloped viruses, spores and/or endospores. The microorganisms can be loosely adhered to the surface or aggregated in a biofilm matrix. The liquid emulsions can be stable over an extended period of time. In some embodiments, the liquid emulsion can withstand boiling, freezing and and/or centrifugation, for example exhibiting nominal changes in emulsion droplet size. In some embodiments, anticipated shelf life can be at least about 1 year to about 3 years. In some embodiments, these emulsions can be suitable for a variety of commercial applications.

The term "antimicrobial", as used herein, describe the ability to inactivate and/or kill greater than or equal to about 99.9% of microbial pathogens, such as Gram-positive and/or Gram-negative bacteria, fungus, spores and/or viruses, in an unspecified timeframe. "Antiseptics" and "sanitizers" are defined as killing greater than or equal to 99.9% of microbial pathogens within about 10 minutes or less, for example as specified by some U.S. government performance standards.

The terms "nanoemulsion" and "miniemulsion" are used to define emulsions in which a mean droplet size is between about 25 nm to about 1000 nm, including for example from about 100 nm to about 600 nm.

In some embodiments, a formulation can comprise about 0.02% to about 1.00% by weight of a monoterpenoid (e.g., thymol, carvacrol, and/or menthol) and/or a polyphenol (e.g., eugenol), a non-ionic surfactant in which the weight ratio of the monoterpenoid and/or the phenol to surfactant is between about 1:5 and about 30:1, a co-solvent of organic compound (such as ethanol) at about 0.25% to about 15% by weight, and/or water. A role of the surfactants and/or organic solvent can be to facilitate a spontaneous emulsification process and/or a long-term thermodynamic stability of the emulsion droplets. Active components, such as thymol and carvacrol, are often available as crystalline solids that are mostly insoluble in water. While pure emulsions of these active components can be made, the pure emulsions can be highly unstable, for example phase separating within hours due to an Ostwald ripening process. Phenolic compounds can be soluble in organic solvents, such as ethanol, diethyl ether and/or acetone, although these organic solvents can generally be harsh, toxic, and/or generally not optimal for consumer use as an antiseptic, disinfectant and/or as food additives.

While there are a variety of surfactants and/or emulsifiers that can be used to stabilize emulsions, for example emulsions comprising phenolic based compounds and/or essential oils, surprisingly, some of these combinations can be antagonistic for antimicrobial properties and/ or shelf life properties of the emulsions. For example, a combination of thymol with a cationic surfactant, such as benzethonium chloride (which is also highly antimicrobial), can decrease the antibacterial activity of thymol, and/or reduce a shelf life property of the combination, for example, by becoming rancid within about three months. Emulsions comprising about 0.0625% by weight of a thyme oil, combined with polysorbate 80 (e.g., Tween 80®), lauric arginate and/or sodium dodecyl sulfate can show reduced antifungal activity, even though the individual components are antifungal. This is completely unexpected and demonstrates not all surfactants are compatible with essential oil derivatives with respect to antimicrobial properties and/or shelf life properties.

Prior art attempts to extend the shelf life of essential oil-based antimicrobial emulsions by adding Ostwald ripening inhibitors, e.g., medium chain length triglycerides (corn oil), were found to adversely impact antimicrobial properties. For example, inclusion of a medium chain length triglyceride increased the shelf life of thyme based emulsions but drastically reduced the antimicrobial effects of the emulsions.

Unexpectedly, not all surfactants can facilitate formation of thermally stable submicron emulsions (e.g., a mean emulsion droplet diameter of less than about 1000 nm). For example, polyethylene glycol can produce micro and/or macroscale emulsions that can exhibit phase segregation. Furthermore, emulsion droplets in the nanoscale tend to contribute to increase the shelf life of the emulsion, by reducing flocculation, aggregation, creaming and/or sedimentation. In some embodiments, miniemulsions can facilitate improved penetration into the skin and/or into rough surface patches, can be more uniformly distributed in solution, and/or can be less viscous than comparable macroemulsions.

In some embodiments, non-ionic surfactants, when combined with phenolic active components, for example in certain ratios, can provide stable self-assembling emulsions, including miniemulsions, which have useful antimicrobial activity. Some example formulations are outlined in Table 1.

In some embodiments, a formulation can advantageously include an emulsion made with extremely low surfactant concentrations, for example less than about 0.1% by weight. In some embodiments, an emulsion can advantageously include a surfactant at less than about 0.01% by weight. In contrast, many common disinfecting products currently available include surfactant concentrations in the about 3% to about 10% weight range, including for disinfecting products having essential oil concentrations at about 1% by weight. For example, a stable nanoemulsion can be made with a thymol concentration of about 0.063%, a surfactant concentration of about 0.0063% and about 1% of a co-solvent (e.g., ethanol), by weight. Other active components (e.g., a monoterpenoid and/or a polyphenol), and/or other co-solvent s (e.g., an organic co-solvent) may be suitable. In some embodiments, an emulsion having such a composition can be surprisingly stable, for example having a monodisperse particle size of ~120 nm. In some embodiments, an emulsion having such a composition can withstand centrifugation, boiling and/or freezing without or substantially without significant phase separation. In some embodiments, emulsions of such a composition can demonstrate minimal size change after about three months of shelf life testing. This low surfactant formulation is highly unexpected and demonstrates a unique quasi-static emulsion state. A formulation comprising such a reduced quantity of a surfactant can represent a 10 to 100-fold reduction in the amount of stabilizing surfactant typically used in essential oil products.

A formulation having a low-surfactant composition can be beneficial, for example by producing a less soapy feel or texture to the product, and/or by reducing the possibility of irritation caused by the surfactant. Many surfactants in cosmetic and/or pharmaceutical use can cause skin irritation and/or other allergic reactions. By substantially reducing the surfactant concentration, the probability for contact dermatitis can be minimized. Economically, the reduced amount of surfactant may reduce cost of product manufacturing.

In another embodiment, a formulation can be advantageously incorporated into a hydrocolloid suspension (e.g., a gel system and/or a paste system). For example, a formulation (e.g., a formulation comprising a nanoemulsion) can be mixed into an existing hydrocolloid suspension. A hydrocolloid suspension can include a variety of components, including but not limited to polysaccharides such as xanthan gum, collagen (e.g., gelatin), petrolatum, combinations thereof, and/or the like. In some embodiments, a mixture of the formulation and the hydrocolloid suspension can have a concentration of an active component (e.g., a phenolic active) between about 0.02% and about 0.5% by weight of the final mixture. Mixtures of formulations and hydrocolloid suspensions can be suitable for a variety of applications, including in wound dressing applications, for example facilitating slow release of the formulation and/or creation of an antimicrobial barrier on a target wound surface.

In some embodiments, water, isotonic saline or a water-based phosphate buffer may be used as the liquid phase carrier, for example with sufficient water to make up 100% by weight of the formulation. Deionized and/or distilled water may be used. A co-solvent may be an organic solvent, including but not limited to, ethanol, methanol, acetone, butanol, chloroform, methyl ethyl ketone, dimethyl sulfoxide (DMSO), ether, carboxylic acids, including, for example, acetic acid or citric acid, and the like, and combinations thereof. A co-solvent can help stabilize the emulsion. Heat energy may be used to form an emulsion where a formulation includes no co-solvent. A formulation for an end-user product can advantageously have a concentration of the co-solvent at less than about 5%, by weight. In some embodiments, a formulation can have a co-solvent at a concentration between about 0.25% to about 1%, by weight. In some embodiments, a formulation can have an increased concentration of a co-solvent, including a concentration of the co-solvent of about 5% to about 50%, by weight, for example to facilitate emulsion stability. The co-solvent can be synthetic and/or naturally extracted. Formulations used in food applications may include an edible co-solvent.

A formulation may include one or more ingredients to enhance the antimicrobial and/or cleaning efficacy of the formulation. For example, a co-surfactant can be used to further improve long-term stability. A chelator, such as ethylenediaminetetraacetic acid (EDTA) and/or citric acid, can be added to bind ions typically found in hard water. These ions may change the surfactant solubility and/or interfere with the antimicrobial activity of the emulsions. A germinating agent may be introduced to more effectively destroy dormant spores and/or endospores. These sporulating agents can encourage the spores to transition into the vegetative cell state, at which point the spore can effectively inactivated by the emulsions. These germinating agents may include amino acids, sugars, ions and/or enzymes.

In some embodiments, a formulation can comprise a scented ingredient and/or a fragrance. Scented ingredients and/or fragrances can be synthetic compounds and/or naturally extracted from floral and/or fruit. In some embodiments, scented ingredients and/or fragrances may be essential oils.

A mechanism of antimicrobial activity for a miniemulsion, including a miniemulsion as described herein, can be based on membrane disruption of the target pathogen. As the miniemulsions can be formed from hydrophobic compounds (e.g., monoterpenoids), they can be highly lipophilic. For example, fusion between the miniemulsions and microbial membranes, and/or the partitioning of the membrane lipids can be responsible for disrupting the membrane integrity, causing intracellular leakage of contents and/or cell death. The lack of an oil and/or lipid component in example formulations can enhance the performance of the active components, since the lipid can act to block the phenolic compound from accessing the cell membrane.

In some embodiments, emulsions as described herein can possess several unique and/or unexpected properties conducive for scale up manufacturing. For example, exemplary formulations with unique ratios of active:surfactant:co-solvent ratio may spontaneously form emulsions (e.g., self-assemble) upon combining the active component, surfactant and co-solvent. Example ranges of ratios and/or concentration ranges include the ratios and/or concentrations as described herein. Outside of the specified exemplary ranges, the mixed components may phase separate (e.g., layering) and/or may not form emulsions. Self-assembly may be driven by favorable thermodynamic conditions. For example, a decrease in surface tension, for example through addition of an appropriate quantity of surfactant, and/or an emulsion having strong interfacial repulsion between emulsion droplets, may facilitate formation of a self-assembling emulsion having extended shelf life properties. Self-assembly may eliminate a need for homogenization, heat application, and/or high pressure and/or high shear processing. This self-assembly process of the emulsion is in direct contrast to currently available nanoemulsion fabrication techniques, which often can require input energy, for example in the form of high frequency sonication and/or homogenization, to form emulsion droplets (e.g., nanosized emulsion droplets). This manufacturing advantage can be especially attractive in the industrial setting, reducing the overall difficulty in scale-up. In some embodiments, emulsions having components within the described ratio ranges and/or concentration ranges can be monodisperse (e.g., PDI<0.5), highly stable and/or can be repeatably manufactured. In some embodiments, accelerated and/or real-time shelf life studies show minimal changes in the emulsion droplet size, for example indicating that the emulsion is monodisperse, and/or demonstrating homogeneous size distribution in the emulsion droplet size. Example active components may be environmentally friendly, and/or may degrade very quickly in the soil and/or waste water run-off.

In some embodiments, the active component is first heated into liquid form and subsequently added to the aqueous solvent phase and homogenized. In other embodiments, the emulsions are prepared by dissolving the active component into the organic co-solvent, and then mixed with a surfactant and water at the specified concentration ranges. In yet another embodiment, the active component, in a liquid form, can be added to the water/co-solvent/surfactant mix directly and then homogenized.

Table 1 shows non-limiting examples of formulations.

TABLE 1

Example Formulations

| Component | Weight/Volume (%) |
|---|---|
| Example 1: Antimicrobial nanoemulsion | |
| Thymol | 0.063 |
| Polysorbate 20 | 0.0063 |
| Ethanol | 1.00 |
| DI Water | 98.9307 |
| Total | 100.00 |
| Example 2: Antimicrobial nanoemulsion | |
| Thymol | 0.063 |
| Sodium laureth sulfate | 0.0063 |
| Ethanol | 1.00 |
| Water | 98.9307 |
| Total | 100.00 |
| Example 3: Antimicrobial nanoemulsion | |
| Carvacrol | 0.063 |
| Polysorbate 20 | 0.0063 |
| Ethanol | 1.00 |
| Water | 98.9307 |
| Total | 100 |
| Example 4: Antimicrobial nanoemulsion | |
| Thymol | 0.063 |
| Citric acid | 1.00 |
| Polysorbate 20 | 0.0063 |
| Ethanol | 1.00 |
| Water | 97.9307 |
| Total | 100.00 |

EXPERIMENTAL EXAMPLES

Antimicrobial susceptibility and accelerated stability testing of example formulations were conducted to assess emulsion properties. Compositions of the example formulations include a ratio of surfactant to active component as listed in Tables 2-5. In some embodiments, the formulations can include ethanol as a co-solvent. For example, a formulation can include a co-solvent (e.g., ethanol) at about 1% by weight. For stability assessment, the mean droplet size of the emulsion as a function of time and processing was measured via dynamic light scattering. The results of these formulations are presented in Table 2 in the form of emulsion particle size and PDI. The results are shown for embodiments in which the emulsion was diluted to give a concentration of active component of 0.063%; similar droplet sizes can be obtained in higher and lower dilutions of the emulsions. For some embodiments, additional stability processing was conducted, as shown in Tables 3-5. These tests included moderate heating (e.g., heating to about 45° C. for about 48 hrs), a freeze thaw cycle (e.g., cycling a temperature of a formulation from about −21 degree C. (° C.) to about 25° C.), and/or centrifugation (e.g., for about 30 min) at 13000 g of the emulsion system. After post-processing, the emulsion particle size was again investigated to look at potential phase separation and instability.

TABLE 2

Example Formulations

| ID# | Active | Surfactant | Ratio of Surfactant:Active | Average Emulsion Particle Size (nm) | PDI |
|---|---|---|---|---|---|
| 1 | Thymol | Polysorbate 20 (e.g., Tween 20 ®) | 1:2 | 616 | 0.52 |
| 2 | Thymol | Polysorbate 20 (e.g., Tween 20 ®) | 1:5 | 139 | 0.46 |
| 3 | Thymol | Polysorbate 20 (e.g., Tween 20 ®) | 1:10 | 135** | 0.30 |
| 4 | Thymol | Sodium dodecyl sulfate (SLS) | 1:2 | 90 | 0.44 |
| 5 | Thymol | SLS | 1:5 | 69 | 0.40 |
| 6 | Thymol | SLS | 1:10 | 157 | 0.29 |
| 7 | Thymol | polyoxyethylene 20 cetyl ether (e.g., Brij 58 ®) | 1:2 | 223 | 0.44 |
| 8 | Thymol | polyoxyethylene 20 cetyl ether (e.g., Brij 58 ®) | 1:5 | 257 | 0.53 |
| 9 | Thymol | polyoxyethylene 20 cetyl ether (e.g., Brij 58 ®) | 1:10 | 162 | 0.74 |
| 10 | Thymol | Polyethylene glycol (e.g., PEG 400) | 1:2 | *n/a | *n/a |
| 11 | Thymol | Polyethylene glycol (e.g., PEG 400) | 1:5 | *n/a | *n/a |
| 12 | Thymol | Polyethylene glycol (e.g., PEG 400) | 1:10 | *n/a | *n/a |
| 13 | Thymol | Octylphenol ethoxylate (e.g., Triton X ®) | 1:2 | *n/a | *n/a |
| 14 | Thymol | Octylphenol ethoxylate (e.g., Triton X ®) | 1:5 | *n/a | *n/a |
| 15 | Thymol | Octylphenol ethoxylate (e.g., Triton X ®) | 1:10 | *n/a | *n/a |
| 16 | Carvacrol | Polysorbate 20 (e.g., Tween 20 ®) | 1:2 | | |
| 17 | Carvacrol | Polysorbate 20 (e.g., Tween 20 ®) | 1:5 | | |
| 18 | Carvacrol | Polysorbate 20 (e.g., Tween 20 ®) | 1:10 | | |
| 19 | Eugenol | Polysorbate 20 (e.g., Tween 20 ®) | 1:2 | *n/a | *n/a |
| 20 | Eugenol | Polysorbate 20 (e.g., Tween 20 ®) | 1:5 | *n/a | *n/a |
| 21 | Eugenol | Polysorbate 20 (e.g., Tween 20 ®) | 1:10 | *n/a | *n/a |

*n/a denotes emulsion size too large to measure with dynamic light scattering or no emulsion formed.
**165 nm with PDI of 0.27 after 3 months storage at 25° C.

TABLE 3

Post Heating of Example Embodiments

| ID# | Active | Surfactant | Ratio of Surfactant:Active | Average Emulsion Particle Size (nm) | PDI |
|---|---|---|---|---|---|
| 1 | Thymol | Polysorbate 20 (e.g., Tween 20 ®) | 1:2 | 292 | 0.45 |
| 2 | Thymol | Polysorbate 20 (e.g., Tween 20 ®) | 1:5 | 108 | 0.53 |
| 3 | Thymol | Polysorbate 20 (e.g., Tween 20 ®) | 1:10 | 123 | 0.24 |
| 4 | Thymol | SLS | 1:2 | 151 | 0.36 |
| 5 | Thymol | SLS | 1:5 | 153 | 0.46 |
| 6 | Thymol | SLS | 1:10 | 144 | 0.75 |
| 7 | Thymol | polyoxyethylene 20 cetyl ether (e.g., Brij 58 ®) | 1:2 | *n/d | — |
| 8 | Thymol | polyoxyethylene 20 cetyl ether (e.g., Brij 58 ®) | 1:5 | *n/d | — |
| 9 | Thymol | polyoxyethylene 20 cetyl ether (e.g., Brij 58 ®) | 1:10 | *n/d | — |

*n/d denotes no data

TABLE 4

Post Freeze of Example Embodiments

| ID# | Active | Surfactant | Ratio of Surfactant:Active | Average Emulsion Particle Size (nm) | PDI |
|---|---|---|---|---|---|
| 1 | Thymol | Polysorbate 20 (e.g., Tween 20 ®) | 1:2 | 202 | 0.41 |
| 2 | Thymol | Polysorbate 20 (e.g., Tween 20 ®) | 1:5 | 99 | 0.60 |
| 3 | Thymol | Polysorbate 20 (e.g., Tween 20 ®) | 1:10 | 109 | 0.30 |
| 4 | Thymol | SLS | 1:2 | 244 | 0.21 |
| 5 | Thymol | SLS | 1:5 | 165 | 0.38 |
| 6 | Thymol | SLS | 1:10 | 197 | 0.61 |
| 7 | Thymol | polyoxyethylene 20 cetyl ether (e.g., Brij 58 ®) | 1:2 | *n/d | — |
| 8 | Thymol | polyoxyethylene 20 cetyl ether (e.g., Brij 58 ®) | 1:5 | *n/d | — |
| 9 | Thymol | polyoxyethylene 20 cetyl ether (e.g., Brij 58 ®) | 1:10 | *n/d | — |

*n/d denotes no data

TABLE 5

Post Centrifugation (e.g., for about 30 min) of Example Embodiments

| ID# | Active | Surfactant | Ratio of Surfactant:Active | Average Emulsion Particle Size (nm) | PDI |
|---|---|---|---|---|---|
| 1 | Thymol | Polysorbate 20 (e.g., Tween 20 ®) | 1:2 | 432 | 0.46 |
| 2 | Thymol | Polysorbate 20 (e.g., Tween 20 ®) | 1:5 | 143 | 0.4 |
| 3 | Thymol | Polysorbate 20 (e.g., Tween 20 ®) | 1:10 | 136 | 0.32 |
| 4 | Thymol | SLS | 1:2 | 152 | 0.26 |
| 5 | Thymol | SLS | 1:5 | 126 | 0.28 |
| 6 | Thymol | SLS | 1:10 | 121 | 0.11 |
| 7 | Thymol | polyoxyethylene 20 cetyl ether (e.g., Brij 58 ®) | 1:2 | 262 | 0.32 |
| 8 | Thymol | polyoxyethylene 20 cetyl ether (e.g., Brij 58 ®) | 1:5 | 214 | 0.32 |
| 9 | Thymol | polyoxyethylene 20 cetyl ether (e.g., Brij 58 ®) | 1:10 | 117 | 0.49 |

In addition to accelerated storage stability treatments, the antimicrobial activity of some embodiments were assessed on a variety of fungus, bacteria and and/or viruses using a time-kill assay under good laboratory practice (GLP) conditions. Table 6 shows a non-exhaustive list of pathogens tested using formulations having the composition of embodiment Example 1, as shown in Table 1. Testing procedures included American Society for Testing and Materials (ASTM) method E1052 (ASTM E1052) suspension test.

TABLE 6

Antimicrobial Testing of Embodiment #1

| Microorganism | Contact Time | Colony-forming units/milliliter (CFU/mL) | % Reduction |
|---|---|---|---|
| B. cereus endospore | Time zero | 5.00E+06 | n/a |
| | 1 minute | 4.00E+06 | 21.569 |
| | 10 minutes | 2.80E+06 | 45.098 |
| C. albicans ATCC 10231 | Time zero | 2.25E+06 | n/a |
| | 1 minute | 2.50E+02 | 99.989 |
| | 10 minutes | <50 | >99.997 |
| E. faecalis (VRE) ATCC 51299 | Time zero | 1.17E+06 | n/a |
| | 1 minute | 3.35E+04 | 97.124 |
| | 10 minutes | 1.50E+06 | 99.987 |
| E. coli ATCC 11229 | Time zero | 3.80E+07 | n/a |
| | 1 minute | 1.42E+04 | 99.963 |
| | 10 minutes | 1.00E+03 | 99.997 |
| P. aeruginosa ATCC 15442 | Time zero | 5.20E+07 | n/a |
| | 1 minute | 3.60E+06 | 93.077 |
| | 10 minutes | 3.40E+04 | 99.935 |
| S. aureus ATCC 6538 | Time zero | 1.47E+07 | n/a |
| | 1 minute | 2.75E+05 | 98.129 |
| | 10 minutes | 8.75E+04 | 99.405 |
| S. aureus (MRSA) ATCC 33592 | Time zero | 1.15E+06 | n/a |
| | 1 minute | 3.00E+02 | 99.974 |
| | 10 minutes | <50 | >99.996 |
| Herpes simplex 1 strain HF | Time zero | 5.1E+05 | n/a |
| | 1 minute | 2.25E+01 | 99.7 |
| | 10 minutes | <1.50E+02 | >99.97 |

Experimental data show multiple miniemulsion embodiments were made that were kinetically stable when subjected to accelerated stability testing. Additionally, some embodiments were tested for antimicrobial activity and were shown to be extremely biocidal within about 1 minute and about 10 minute time spans. These results demonstrate near surfactant-free formulations in which the antimicrobial properties of the native phenolic compound can be preserved in a surprisingly stable manner.

Figure 2:
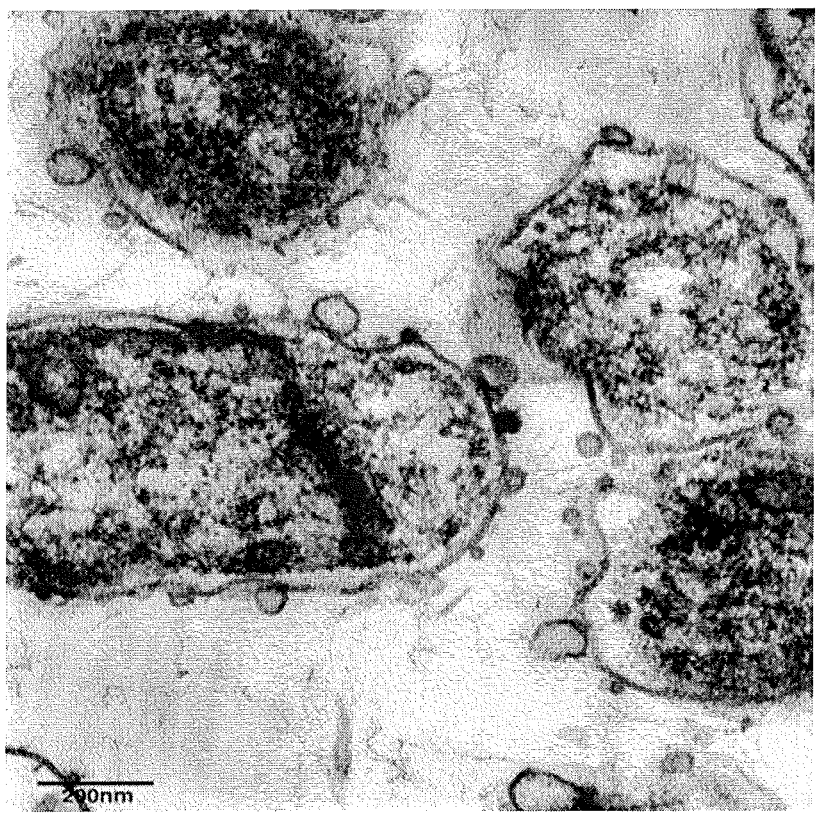
FIG. 2 is a transmission electron micrograph showing the mechanism of action of thymol based emulsions in which membrane emulsification and lysis of *E. coli* was evident at a thymol concentration of 0.10%.

Emulsion ID#3, which contains thymol and polysorbate 20 in a 10:1 ratio, respectively, was evaluated using negative staining transmission electron microscopy (FIG. 1) and was found to have an average emulsion particle size of about 135 nm, as corroborated by dynamic light scattering. The effect of the main active component, thymol, on pathogenic E. coli was visualized using transmission electron microscopy (FIG. 2). With reference to FIG. 2, pathogenic E. coli exposed to a pure thymol emulsion at 0.10% concentration exhibits signs of immediate bacteriolysis and membrane damage. These results clearly demonstrate the membrane perturbing effects of thymol.

In addition to assays that describe the antimicrobial activity of planktonic (free floating) microorganisms, experiments assessing the effects of these emulsions on biofilms were also performed. These tests were conducted on romaine lettuce and blueberries inoculated with several food-borne bacteria in order to simulate agricultural applications. Briefly, these experiments first involved inoculating lettuce and blueberries with E. coli 0157:H7, Salmonella spp., and Listeria monocytogenes. The samples were then incubated at room temperature for 1.5 hours to allow for biofilm formation. Following incubation, the lettuce or blueberry samples were exposed to several variants of the emulsions sanitizers for 1 minute. After emulsion treatment, the vegetable/fruit samples were neutralized and homogenized and serially plated onto selective media for pathogen identification and enumeration. These biofilm antimicrobial tests were done at both 25° C. and at 4° C. The experimental data are shown below. All emulsions listed were used at 0.10% active thymol concentration:

| | Pathogen | Starting Conc. (CFU) | Log Reduction (after 1 min) | Error (log) |
|---|---|---|---|---|
| Romaine Lettuce Treatment at 25° C. | | | | |
| Water | Salmonella spp | 1.02E+06 | 0.76 | 0.29 |
| Emulsion ID#3 | Salmonella spp | 1.02E+06 | 1.68 | 0.31 |

|  | Pathogen | Starting Conc. (CFU) | Log Reduction (after 1 min) | Error (log) |
|---|---|---|---|---|
| Emulsion ID#6 | *Salmonella* spp | 1.02E+06 | 1.68 | 0.34 |
| Emulsion #6 w/ 0.2% citric acid | *Salmonella* spp | 1.02E+06 | 2.22 | 0.34 |
| Water | *E. coli* O157:H7 | 1.32E+06 | 1.74 | 0.12 |
| Emulsion #3 | *E. coli* O157:H7 | 1.32E+06 | 1.82 | 0.26 |
| Emulsion #6 | *E. coli* O157:H7 | 1.32E+06 | 2.34 | 0.20 |
| Emulsion #6 w/ 0.2% citric acid | *E. coli* O157:H7 | 1.32E+06 | 2.36 | 0.14 |
| Water | *Listeria monocytogenes* | 7.34E+03 | 0.75 | 0.22 |
| Emulsion #3 | *Listeria monocytogenes* | 7.34E+03 | 1.55 | 0.23 |
| Emulsion #6 | *Listeria monocytogenes* | 7.34E+03 | 1.48 | 0.28 |
| Emulsion #6 w/ 0.2% citric acid | *Listeria monocytogenes* | 7.34E+03 | 1.65 | 0.24 |
| Blueberry Treatment at 4° C. | | | Log | |
| Water | *Salmonella* spp | 1.17E+06 | 0.85 | 0.16 |
| Emulsion #3 | *Salmonella* spp | 1.17E+06 | 2.03 | 0.23 |
| Emulsion #6 | *Salmonella* spp | 1.17E+06 | 1.71 | 0.25 |
| Emulsion #6 w/ 0.2% citric acid | *Salmonella* spp | 1.17E+06 | 2.41 | 0.25 |
| Water | *E. coli* O157:H7 | 9.22E+05 | 0.78 | 0.10 |
| Emulsion #3 | *E. coli* O157:H7 | 9.22E+05 | 1.26 | 0.11 |
| Emulsion #6 | *E. coli* O157:H7 | 9.22E+05 | 1.38 | 0.14 |
| Emulsion #6 w/ 0.2% citric acid | *E. coli* O157:H7 | 9.22E+05 | 1.55 | 0.12 |
| Water | *Listeria monocytogenes* | 3.17E+05 | 1.41 | 0.32 |
| Emulsion #3 | *Listeria monocytogenes* | 3.17E+05 | 1.13 | 0.25 |
| Emulsion #6 | *Listeria monocytogenes* | 3.17E+05 | 1.32 | 0.26 |
| Emulsion #6 w/ 0.2% citric acid | *Listeria monocytogenes* | 3.17E+05 | 1.88 | 0.21 |
| Blueberry Treatment at 25° C. | | | Log | |
| Water | *Salmonella* spp | 1.82E+06 | 1.37 | 0.13 |
| Emulsion #3 | *Salmonella* spp | 1.82E+06 | 2.06 | 0.21 |
| Emulsion #6 | *Salmonella* spp | 1.82E+06 | 2.47 | 0.21 |
| Emulsion #6 w/ 0.2% citric acid | *Salmonella* spp | 1.82E+06 | 1.95 | 0.21 |
| Water | *E. coli* O157:H7 | 1.32E+06 | 0.51 | 0.10 |
| Emulsion #3 | *E. coli* O157:H7 | 1.32E+06 | 1.64 | 0.12 |
| Emulsion #6 | *E. coli* O157:H7 | 1.32E+06 | 1.56 | 0.21 |
| Emulsion #6 w/ 0.2% citric acid | *E. coli* O157:H7 | 1.32E+06 | 1.32 | 0.20 |
| Water | *Listeria monocytogenes* | 8.29E+05 | 1.41 | 0.25 |
| Emulsion #3 | *Listeria monocytogenes* | 8.29E+05 | 2.00 | 0.26 |
| Emulsion #6 | *Listeria monocytogenes* | 8.29E+05 | 2.12 | 0.29 |
| Emulsion #6 w/ 0.2% citric acid | *Listeria monocytogenes* | 8.29E+05 | 2.65 | 0.25 |

Results showed that the emulsions had between 1-3 logs (or 90-99.9%) of reduction on food borne biofilms when washed for 1 minute. This treatment was significantly better than washing with water, which generally provided less than 1 log of reduction. The data was consistent on both blueberries and romaine lettuce. These efficacy values are comparable to chlorine based sanitizers used at 10-50 ppm. Moreover, the addition of 0.2% citric acid also slightly improved the antimicrobial effectiveness of the emulsions, suggesting enhanced activity in acidic environments. The emulsions were slightly better performing at room temperature vs 4° C. Overall, the data demonstrate that these emulsions can be used as agricultural sanitizers and in biofilm remediation.

Although this disclosure has been provided in the context of certain embodiments and examples, it will be understood by those skilled in the art that the disclosure extends beyond the specifically disclosed embodiments to other alternative embodiments and/or uses of the embodiments and obvious modifications and equivalents thereof. In addition, while several embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the disclosed embodiments. Thus, it is intended that the scope of the disclosure herein provided should not be limited by the particular embodiments described above. Rather, the intention is to cover all modifications, equivalents, and alternatives falling within the scope of the disclosure as defined by the appended claims.

What is claimed is:

1. A self-assembling antimicrobial formulation comprising:
    an effective amount of an active component, the active component comprising thymol, wherein thymol is present at a concentration of 0.02% to 1% by weight;
    a non-ionic or anionic surfactant selected from the group consisting of polysorbates and sodium laureth sulfate, wherein the non-ionic or anionic surfactant is present at a concentration of 0.0015% to 0.1% by weight;
    an organic co-solvent selected from the group consisting of ethanol, acetic acid, and citric acid, wherein the co-solvent is present at a concentration of 0.2 to 2% by weight; and
    water, wherein the weight ratio of thymol to the nonionic or anionic surfactant is 10:1 to 5:1, and
    wherein the formulation is a self-assembling emulsion having a mean emulsion droplet size from about 25 nm to 900 nm.

2. The antimicrobial formulation of claim 1, wherein the antimicrobial formulation is effective against microorganisms selected from the group consisting of *Escherichia coli, Pseudomonas aeruginosa, Staphylococcus aureus* MRSA strain, *Enterococcus faecalis* VRE strain, *Candida albicans*, Herpes simplex 1, *Salmonella typhimurium* and *Listeria monocytogenes*.

3. The antimicrobial formulation of claim 2, wherein the formulation inactivates the microorganisms by a factor of greater than or equal to a 3-log reduction within about 10 minutes.

4. The antimicrobial formulation of claim 1, wherein the thymol is present at a concentration of about 0.05% to about 0.10% by weight.

5. The antimicrobial formulation of claim 1, wherein the surfactant is present at a concentration of about 0.005% to about 0.01% by weight.

6. The antimicrobial formulation of claim 1, wherein the organic co- solvent is present at a concentration of about 0.25% to about 1% by weight.

7. The antimicrobial formulation of claim 1, wherein the antimicrobial formulation is delivered in an emulsion form.

8. The antimicrobial formulation of claim 1, wherein a mean emulsion droplet size of the emulsion is about 25 nm to about 500 nm.

9. The antimicrobial formulation of claim 1, wherein a mean emulsion droplet size of the emulsion is about 100 nm to about 600 nm.

10. The antimicrobial formulation of claim 1 further comprising a chelating agent.

11. The antimicrobial formulation of claim 10, wherein the chelating agent comprises at least one selected from the group consisting of EDTA and citric acid.

12. The antimicrobial formulation of claim 1 further comprising a spore germinating agent.

13. The antimicrobial formulation of claim 1, wherein the antibacterial formulation is used for at least one of a surface disinfectant, an antiseptic preparation for wounds, and an agricultural disinfectant.

14. The antimicrobial formulation of claim 1, wherein the antibacterial formulation is implemented in a liquid form.

15. The antimicrobial formulation of claim 1, wherein the antibacterial formulation is incorporated into a hydrocolloid suspension.

16. The antimicrobial formulation of claim 1, wherein the weight ratio of active component to the non-ionic or anionic surfactant is 10:1.

17. The antimicrobial formulation of claim 16, wherein the active component is present at a concentration of about 0.063% to about 0.0315% by weight.

18. The antimicrobial formulation of claim 1, wherein the surfactant is selected from the group consisting of polysorbate 20 and sodium laureth sulfate.

19. A product comprising the self-assembling antimicrobial formulation of claim 1 selected from the group consisting of cleaning solutions, disinfectants, sanitizers, antiseptics, wound care preparations, agricultural sprays or rinses, fruit and vegetable sprays for home use, wipes, and personal care products.

20. A method for reducing viable microorganisms on an object, comprising contacting the object with an effective amount of the antimicrobial formulation of claim 1.

21. The method of claim 20, wherein the object comprises a hard surface, biologic tissue, or foodstuff.

22. A self-assembling antimicrobial formulation consisting of:
    thymol, wherein thymol is present at a concentration of 0.02% to 1% by weight;
    a non-ionic or anionic surfactant selected from the group consisting of polysorbates and sodium laureth sulfate, wherein the non-ionic or anionic surfactant is present at a concentration of 0.0015% to 0.1% by weight;
    an organic co-solvent selected from the group consisting of ethanol, acetic acid, and citric acid, wherein the co-solvent is present at a concentration of 0.2 to 2% by weight; and
    water, wherein the weight ratio of thymol to the nonionic or anionic surfactant is 10:1 to 5:1, and
    wherein the formulation is a self-assembling emulsion having a mean emulsion droplet size from about 25 nm to 900 nm.

* * * * *